United States Patent [19]

Stephens

[11] Patent Number: 4,986,274

[45] Date of Patent: Jan. 22, 1991

[54] FETAL ANATOMIC SEX ASSIGNMENT BY ULTRASONOGRAPHY DURING EARLY PREGNANCY

[76] Inventor: John D. Stephens, 14171 Stanford Ct., Los Altos Hills, Calif. 94022

[21] Appl. No.: 453,123

[22] Filed: Dec. 4, 1989

Related U.S. Application Data

[63] Continuation of Ser. No. 372,234, Jun. 26, 1989, abandoned, and a continuation of Ser. No. 282,824, Dec. 7, 1988, abandoned, which is a continuation of Ser. No. 65,128, Jun. 19, 1987, abandoned, which is a continuation of Ser. No. 914,568, Oct. 2, 1986, abandoned, which is a continuation of Ser. No. 825,781, Feb. 3, 1986, abandoned, which is a continuation of Ser. No. 662,877, Oct. 19, 1984, abandoned.

[51] Int. Cl.$^5$ .............................................. A61B 8/14
[52] U.S. Cl. ............................................... 128/660.07
[58] Field of Search ..................... 128/660.07–660.10, 128/661.01

[56] References Cited

U.S. PATENT DOCUMENTS

| | | | |
|---|---|---|---|
| 3,973,235 | 8/1976 | Van Der Burgt | 128/660 |
| 3,990,296 | 11/1976 | Erikson | 128/660 |
| 4,233,988 | 11/1980 | Dick et al. | 128/660 |
| 4,448,201 | 5/1984 | Matsumoto | 128/660 |
| 4,478,084 | 10/1984 | Hassler et al. | 128/660 |
| 4,520,830 | 6/1985 | Flanagan, III | 128/660 |

FOREIGN PATENT DOCUMENTS 2418472  10/1979  France .................................. 128/660

OTHER PUBLICATIONS

Whittingham, "A Multiple Transducer System for Heart, Abdominal and Obstetric Scanning", Proceedings of the 2nd European Congress on Ultrasonics in Medicine, Munich, Germany, 12-16 May, 1975, pp. 59-66.

(List continued on next page.)

Primary Examiner—Ruth S. Smith
Attorney, Agent, or Firm—William C. Milks, III

[57] ABSTRACT

A method and apparatus are disclosed for fetal anatomic sex assignment by ultrasound during early pregnancy based on pattern recognition that allows identification of external genitalia during the gestational age range of 12 to 14 weeks. The pattern recognition derives from knowledge of the embryology of the developing external genitalia of the fetus and the relationship between embryologic events and recognizing patterns specific for male and female obtained by ultrasonic imaging. Fetal anatomic sex has been accurately diagnosed using high resolution digital linear-array real-time ultrasound in over 500 pregnancies that were scheduled for ultrasound except for detected cases of sex reversal, sex chromosome mosaicism, prior to genetic amniocentesis, and ambiguous sex chromosomes, except as noted, ultrasonic imaging of the penile or clitoral structure corresponded to later sex determination by karyotype. Imaging of the external genitalia can be included as part of a complete fetal anatomic survey, which includes gestational age dating and inspection for gross abnormalities. Sex assignment requires 30 seconds to 10 minutes. Fetal anatomic sex assignment can be performed by ultrasound early in pregnancy, that is, during the twelfth to fourteenth weeks from the last menstrual period of the mother, yet the results are as accurate as those obtained by chromosome analysis from genetic amniocentesis which can be safely performed only after the sixteenth week of pregnancy. Fetal anatomic sex assignment is particularly useful in genetic counseling with regard to X-linked disorders and can be clinically important when either sex reversal, sex chromosome mosaicism, or ambiguous sex chromosomes are detected by prenatal diagnosis. Other features are also disclosed.

20 Claims, 4 Drawing Sheets

OTHER PUBLICATIONS

McDicken et al., "An Ultrasonic Real-Time Scanner with Pulsed Doppler and T-M Facilities for Foetal Breathing and other Obstetrical Studies", Ultrasound in Med. & Biol, vol. 5, No. 4, 1979, pp. 333-339.

Holm et al., "A New Mechanical Real-Time Ultrasonic Contact Scanner", Ultrasound in Med. & Biol., vol. 2, No. 1, Oct. 1975, pp. 19-23.

Takeuchi, "An Investigation of a Spread Energy Method for Medical Ultrasound Systems", Ultrasonics, vol. 17, No. 5, Sep. 1979, pp. 219-224.

Ophir et al., "Digital Scan Converters in Diagnostic Ultrasound Imaging", Proceedings of the IEEE, vol. 67, No. 4, Apr. 1979, pp. 654-664.

Maginness, "Methods and Terminology for Diagnostic Ultrasound Imaging Systems", Proceedings of the IEEE, vol. 67, No. 4, Apr. 1979, pp. 641-653.

Soldner et al., "The Vidoson 735-A New Real-Time Scanner for Sonography", Electromedica 3, Apr. 1977, pp. 107-112.

Dunne et al., "Sonographic Determination of Fetal Gender Before 25 Weeks Gestation", AKR 140: 741-743, Apr. 1, 1983.

GESTATIONAL WEEKS (LMP)
10 - 12      12 - 14
MALE
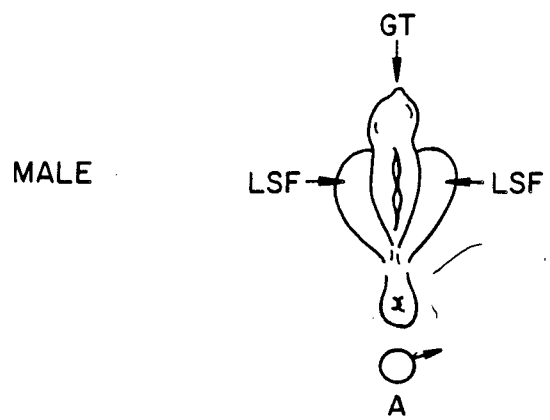
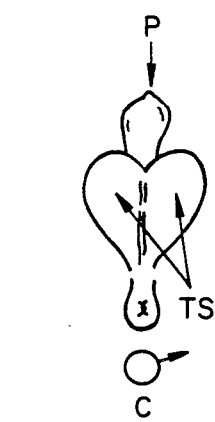
A      C
FEMALE
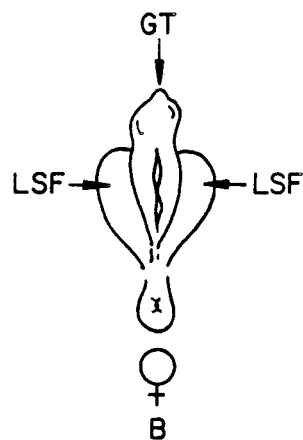
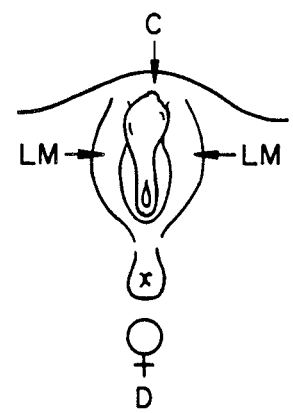
B      D
FIG._1.

SCAN PLANES OF ORIENTATION
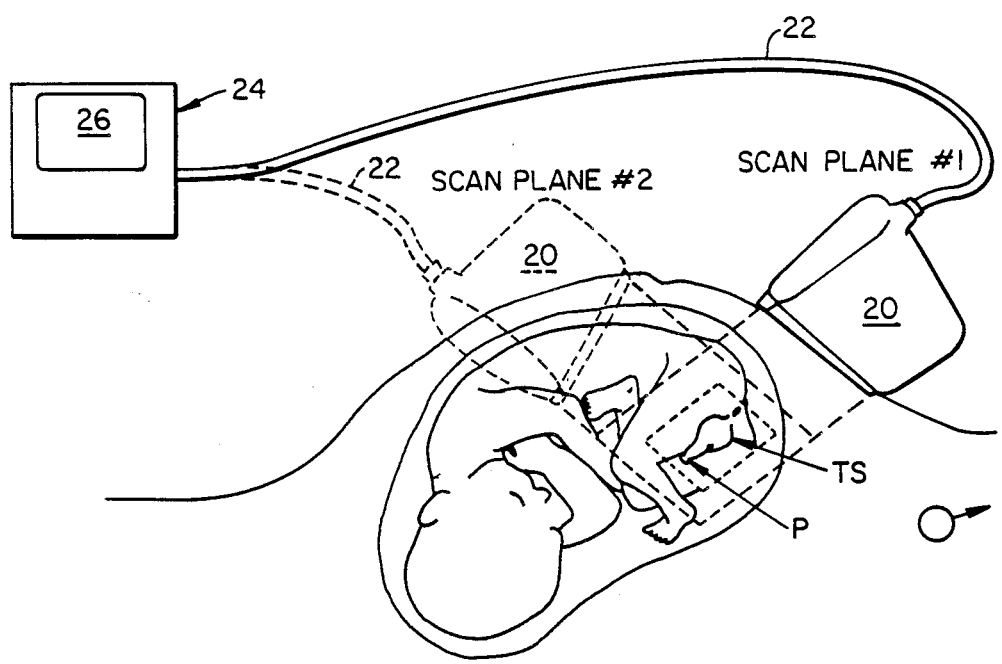
FIG._2.

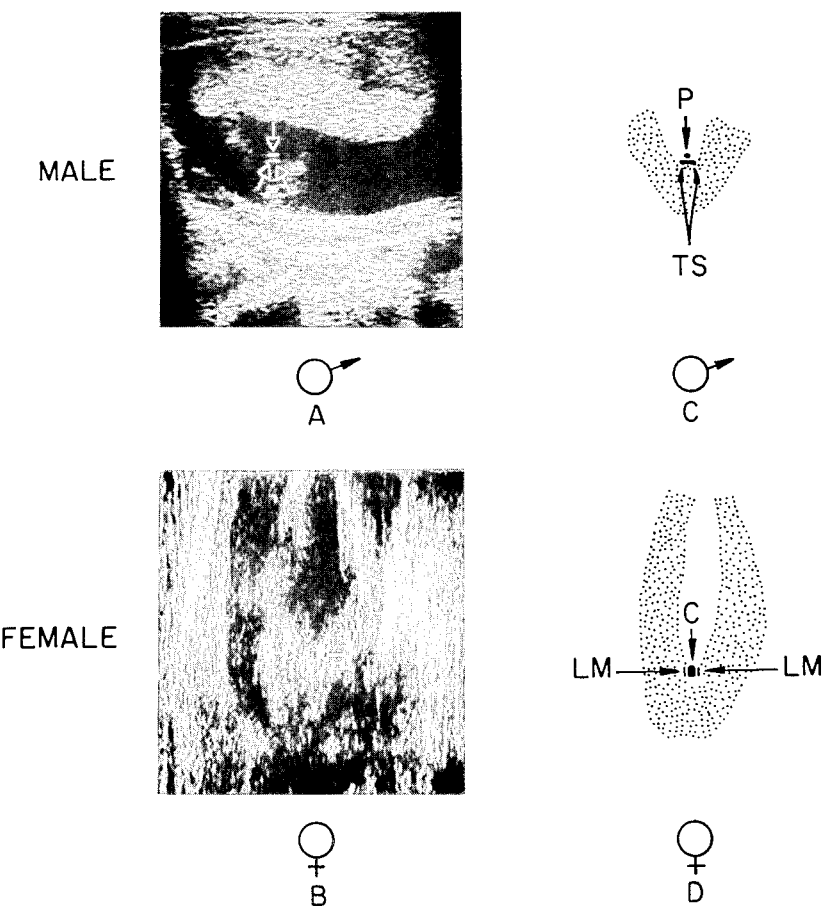
FIG._3.

SCAN PLANE #2
MALE
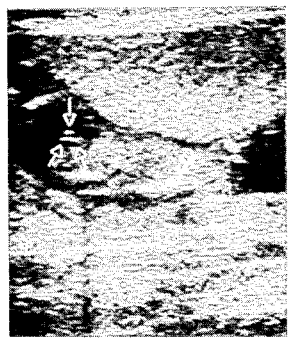
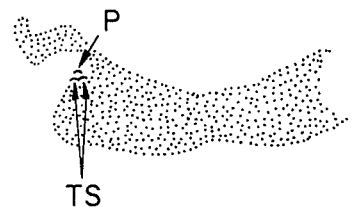
A
C
FEMALE
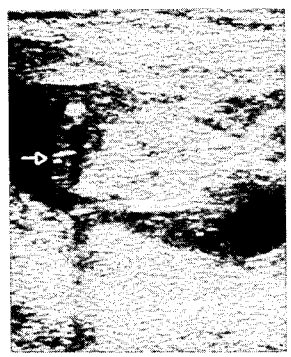
B
D
FIG._4.

FETAL ANATOMIC SEX ASSIGNMENT BY ULTRASONOGRAPHY DURING EARLY PREGNANCY

This is a continuation of application Ser. No. 07/372,234, filed June 26, 1989, now abandoned which is a continuation of application Ser. No. 282,824, filed Dec. 7, 1988, now abandoned which is a continuation, of application Ser. No. 065,128, filed June 19, 1987, now abandoned. which is a continuation of application Ser. No. 06,914,568, filed Oct. 2, 1986, now abandoned which is a continuation of application Ser. No. 06/825,781, filed Feb. 3, 1986, now abandoned which is a continuation of application Ser. No. 06,662,877, filed 10/19/84, now abandoned which is a continuation of application Ser. No. 06/662,877, filed 10/19/84, now abandoned.

BACKGROUND OF THE INVENTION

This invention relates to ultrasonography and, more particularly, to medical techniques which employ ultrasonography. Specifically, the invention is directed to the use of ultrasonic imaging for assigning the anatomic sex of a human fetus during early pregnancy, that is, in the period between the twelfth week and the fourteenth week of gestation.

Technological progress continues to improve the spatial resolution of images obtained using linear-array real-time ultrasound in obstetrical genetics. The change from analog to digital ultrasound systems has contributed to this improvement. With the improvement in resolution in digital linear-array real-time ultrasound systems has come marked improvement in identification of specific parts of fetal anatomy at an increasingly earlier stage of gestation.

The use of ultrasound, or high-frequency sound waves, to produce an image on a screen of a developing fetus and surrounding tissues has increased dramatically in recent years, not only in hospitals, but in doctors' offices. A panel recently convened by the National Institutes of Health concluded that there are more than two dozen medical reasons which warrant the use of ultrasound scans in some cases, including the detection of abnormalities in a fetus, when a doctor has evidence that a medical problem exists; the detection of the presence of twins; the collection of information for the evaluation of fetal growth, activity, and position; and the determination of fetal age for better management of the pregnancy. National Institutes of Health, Consensus Development Conference Consensus Statement, "The Use of Diagnostic Ultrasound Imaging in Pregnancy," Feb. 6–8, 1984.

Heretofore, ultrasound has been used in the area of prenatal medical diagnosis primarily to assess the gestational age, the location of the fetus, and the location of the placenta (afterbirth) in association with the performance of genetic amniocentesis by needle aspiration of amniotic fluid. More recently, it has been used to detect fetal deformities and other structural genetic problems. Ultrasound scans have been used, for example, to ascertain whether or not a fetus is growing properly according to measurement milestones. It has been possible to identify the fetus with a structural defect of growth by assessing limb development, thereby diagnosing short limb dwarfism syndromes, such as prenatal diagnosis of lethal osteogenesis imperfecta.

Knowing the fetus' sex, however, can also be important if a family has a history of genetic disease linked to the X chromosome, which along with the Y chromosome determines sex. Genetic diseases, such as hemophilia A (a bleeding disorder), chronic granulomatous disease, and Lesch-Nyhan disease, that only affect males, are linked to the X chromosome. If a family has a history of the disease, it is desirable to ascertain whether the fetus is a male or a female. In the case of a male fetus, further studies can be performed to determine whether or not the fetus possesses the gene that causes the disorder, such as hemophilia A, for example.

In the case of X-linked disorders, some of which can be prenatally diagnosed by chemical tests but others of which cannot yet be diagnosed, being able to identify the sex of the fetus also has important consequences in terms of the patient interview interaction called genetic counseling. The ability to identify the fetus developing as a female, which cannot be affected even if it is carrying the gene for the disorder, provides the mother with the information she needs to feel reassured with continuation of the pregnancy knowing that she will not bear an affected infant.

Generally, a fetus' sex has heretofore been determined by the in vitro technique known as genetic amniocentesis. Genetic amniocentesis requires the removal of fetal cells from the fluid that surrounds the fetus and cannot safely be performed before the sixteenth week of gestation. Genetic amniocentesis can only be achieved by inserting a large bore (20–22 gauge) needle through the mother's abdomen to withdraw fetal cells. It is known to be associated with an incidence of spontaneous abortion in about one procedure in every 200 cases.

In view of the risks to the mother and the fetus posed by the invasive procedure required by genetic amniocentesis and in light of the aforementioned advances in digital linear-array real-time ultrasound systems, various researchers have investigated the use of ultrasonography in determining fetal sex. Several researchers have published results of sex determination using ultrasound, generally in the developmental stages of pregnancy beyond the fourteenth week. See, for example, Stocker, J., and Evans, L., "Fetal Sex Determination by Ultrasound," Obstet, Gynecol. 50:462 (1977); Conti, M., Plicchi, G., and Altobelli, L., "Accurate Sexing With the Aid of the Real Time Ultrasonography," IRCS Med. Sci. 7:108 (1979); Le Lann, D., Schioceht, F., Heintz, M., et al., "Antenatal Diagnosis of the Sex of the Fetus by Diagnostic Ultrasound (Echograpohy)," J. Gynecol. Obstet. Biol. Reprod. (Paris) 8:315 (1979); DeLaFuente P Olaizola J. I., Iglesias, E., et al., "Diagnosis of the Fetal Sex by Ultrasonography," Clin. Invest. Gynecol. Obstet. 6:223 (1979); Shalev, E., Weiner E. Zuckerman H. "Ultrasound Determination of Fetal Sex," Am J Obstet. Gynecol. 5:141, 582–583 (Nov. 1, 1981); and Dunne, M. L., Cunat, J. S., "Sonographic Determination of Fetal Gender Before 25 Weeks Gestational Age," A. J. R. 140:741–743 (1983).

In the reports of fetal sex determination by ultrasound, the accuracy reported has not been impressive. Determination of female sex has been performed by exclusion of male sex. Furthermore, the earliest time for accurate determination of sex has been reported as being the twenty-sixth week of gestation, thus precluding clinical use of this technique for diagnosis of recessive X-linked disorders. In one report of 227 mothers examined during and after the twentieth week of pregnancy, fetal sex was determined only in 44 percent of the cases with an 87 percent accuracy rate. In a further report on 381 mothers in whom an attempt was made to determine fetal sex in all gestations at or beyond the twentieth week, an accuracy of 100 percent was obtained for fetuses designated as male and confirmed as male at delivery. However, the accuracy of determination of female sex was 97 percent. Shalev, E., Weiner, E., Zuckerman, H., "Ultrasound Determination of Fetal Sex," Am. J. Obstet. Gynecol. 5:141, 582–583 (1981).

A recent report of fetal sex determination by ultrasound indicates improvement both in accuracy and at earlier stages of gestation. Dr. Jason C. Birnholz, however, achieved only 69 percent accuracy in determining the sex of 855 fetuses after 15 weeks of pregnancy, which he believed could be imaged well enough with ultrasound for sex to be determined. That is, the determination of sex by Birnholz required that an ultrasonic image of the fetal external genitalia appear in a mature stage of development (i.e., that the fetal external genitalia could be visualized as being fully formed) before sex was assigned. Birnholz, J. C., "Determination of Fetal Sex," N. Engl. J. Med. 309:942–944 (1983), and Larry Thompson, "Technique Shows Sex of Fetus at 14 Weeks," *San Jose Mercury News*, Thursday, Oct. 20, 1983, pages 1A, 9A. Natsuyama, E., "Sonographic Determination of Fetal Sex From Twelve Weeks of Gestation," Am. J. Obstet. Gynecol. 7:149, 748–757 (Aug. 1, 1984), purports to show accurate fetal sexing from 12 to 40 weeks of gestation. However, the accuracy in early pregnancy from 12 to 14 weeks was only as high as about 85 percent. Only by the demonstration of 100 percent accuracy within an early prenatal diagnosis gestational age range can consideration be given to the technique of fetal anatomic sex assignment by ultrasonography becoming complementary to, and in selected situations serve as a replacement for, genetic amniocentesis for fetal sex determination.

SUMMARY OF THE INVENTION

The invention provides a method and apparatus for assigning the anatomic sex of a fetus during early pregnancy in the gestational age range from the twelfth week to the fourteenth week using ultrasound. The ultrasonic fetal anatomic sex assignment method and apparatus in accordance with the invention provide the ability to not only perform fetal anatomic sex assignment at this early stage of pregnancy, but also to perform it with the same accuracy as achievable heretofore only by the use of genetic amniocentesis during the fourth month of pregnancy.

In accordance with the invention, a method and apparatus are provided for assigning the anatomic sex of a fetus by the end of the fourteenth week of pregnancy. Generally, the ultrasonic fetal anatomic sex assignment method and apparatus in accordance with the invention can accurately identify a male fetus from the twelfth week of gestational age by a single ultrasound visualization study. A female fetus is identified accurately by the end of the fourteenth week and preferably includes two ultrasound visualization studies, one during the beginning of the twelfth week and the second two weeks later so that both studies are performed within the twelfth week to fourteenth week of gestation. The ultrasonic fetal anatomic sex assignment method and apparatus in accordance with the invention are based on pattern recognition derived from ultrasonic imaging.

In accordance with one aspect of the invention, a method for assigning the anatomic sex of a fetus during the twelfth week to the fourteenth week of pregnancy is provided. The method comprises the steps of: ultrasonically imaging the genital area of the fetus with the genital structure visualized in a transverse ultrasonic scan plane; diagnosing a male fetus by identifying the male external genitalia as a two component structure comprised of a bright single echo which represents the penis and two less bright echoes side-by-side, visualized at a distance from the penis, which represent the fused labio-scrotal folds and evidence the early stage of formation of the testicle sac; and diagnosing a female fetus by identifying the female external genitalia as a three component structure comprised of a rectangular echo located between two parallel linear echoes. Additionally, or alternatively, the method comprises the steps of ultrasonically imaging the genital area of the fetus in a longitudinal ultrasonic scan plane; diagnosing a male fetus by identifying the male external genitalia as a two component structure comprised of a bright single echo having an axis at substantially a right angle to the axis of the spinal column, which represents the penis, and two less bright echoes side-by-side, visualized at a distance from the penis, which represent the fused labio-scrotal folds and evidence the early stage of formation of the testicle sac; and diagnosing a female fetus by identifying the female external genitalia as a rectangular structure comprised of a prominent echo which is in the same line of continuity as the lower abdominal wall and protrudes out from the pubic region pointing in a direction which maintains an orientation parallel to the axis of the spinal column, which represents the clitoris.

In accordance with another aspect of the invention, apparatus is provided for assigning the anatomic sex of a fetus during the twelfth week to the fourteenth week of pregnancy. The apparatus comprises: means for ultrasonically imaging the genital area of the fetus with the genital structure visualized in a transverse ultrasonic scan plane; a male fetus being diagnosed by identifying the male external genitalia as a two component structure comprised of a bright single echo which represents the penis and two less bright echoes side-by-side, visualized at a distance from the penis, which represent the fused labio-scrotal folds and evidence the early stage of formation of the testicle sac; and a female fetus being diagnosed by identifying the female external genitalia as a three component structure comprised of a rectangular echo located between two parallel linear echoes. Additionally, or alternatively, the apparatus comprises means for ultrasonically imaging the genital area of the fetus in a longitudinal ultrasonic scan plane; a male fetus being diagnosed by identifying the male external genitalia as a two component structure comprised of a bright single echo having an axis at substantially a right angle to the axis of the spinal column, which represents the penis, and two less bright echoes side-by-side, visualized at a distance from the penis, which represent the fused labio-scrotal folds and evidence the early stage of formation of the testicle sac; and a female fetus being diagnosed by identifying the female external genitalia as a rectangular structure comprised of a prominent echo which is in the same line of continuity as the lower abdominal wall and protrudes out from the pubic region pointing in a direction which maintains an orientation parallel to the axis of the spinal column, which represents the clitoris.

Use of the ultrasound capability in accordance with the invention in the 12 to 14 week gestational age range enables a prenatal diagnosis ultrasonologist the opportunity to widen the scope of medical diagnostic evaluations. This examination can be conducted not only to exclude abnormalities of the fetus, assess the growth of the fetus, determine the position of the placenta, and verify the accuracy of the due date to allow better management of the pregnancy, for example, but also to determine the sex of the fetus as part of the routine assessment of the anatomy of the fetus for other purposes.

Diagnosis of fetal sex in the early second trimester of pregnancy provides an aid in genetic counseling in connection with X-linked disorders for which there is no specific biochemical prenatal test, such as Duchenne muscular dystrophy and X-linked hydrocephalus, or disorders X-linked for which there is a specific biochemical prenatal test, such as adrenoleukodystrophy, Hunter's syndrome, and hemophilia A. A mother and fetus can be spared the risks of more invasive procedures, such as genetic amniocentesis and fetoscopy, together with sparing the mother the period of time of uncertainty awaiting chromosome analysis results if the fetus is a female, and the more invasive procedures are considered only if the fetus is a male.

In addition, visualization of the fetal external genitalia can be useful in the diagnosis of sex chromosome mosaicism when amniocyte karyotyping shows both an XY and an XX or XO cell line. Visualization of external genitalia can clarify the genetic counseling in certain situations where there are ambiguous sex chromosomes. Ultrasound can provide evidence of female development by demonstration of a female phenotype in the fetus at risk for sex reversal in the form of testicular feminization. It is of potential benefit where the developing fetus is at risk for ambiguous external genitalia.

BRIEF DESCRIPTION OF THE DRAWINGS

The above and other features of the invention and the concomitant advantages will be better understood and appreciated by those skilled in the art in view of the description of the preferred embodiments given below in conjunction with the accompanying drawings. In the drawings:

FIG. 1 is a diagrammatic representation of the embryological process of male/female differentiation by the process of labio-scrotal fold fusion (LM-labia majora, LSF-labio-scrotal fold, TS-testicle sac, P-penis, C-clitoris, GT-genital tubercle);

FIG. 2 is a schematic drawing which demonstrates transducer placements for obtaining ultrasonic fetal anatomic sex assignment of a fetus, for example, a male fetus, by utilizing different ultrasonic scan planes of orientation (TS-testicle sac, P-penis);

FIG. 3 is a schematic representation to explain the ultrasonographic photographs showing the external genitalia of male and female fetuses in the fourteenth week of gestation in ultrasonic scan plane #1 shown in FIG. 2 (TS-testicle sac, P-penis, LM-labia majora, C-clitoris); and FIG. 4 is a schematic representation to explain the ultrasonographic photographs showing the external genitalia of male and female fetuses in the fourteenth week of gestation in ultrasonic scan plane #2 shown in FIG. 2 (TS-testicle sac, P-penis, C-clitoris).

DESCRIPTION OF THE PREFERRED EMBODIMENTS

An understanding of ultrasonic fetal anatomic sex assignment in accordance with the invention can be derived from an explanation of the embryological events of external genitalia sex differentiation. See Moore, K. L., *The Developing Human*, Second Edition, page 241, FIG. 13-20, Publisher W. B. Saunders (1977). This will be described in more detail shortly in connection with FIG. 1.

Embryologically, a male fetus is indistinguishable from a female fetus in the indifferent stage during the tenth to twelfth weeks of gestation from the last menstrual period of the mother. During the twelfth to fourteenth weeks of gestation, however, a fetus which is genetically determined by its chromosome morphology to become a male undergoes significant change in the morphology of the external genitalia. The labio-scrotal folds fuse to form the primitive testicle sac. The genital tubercle destined to become the penis skews away from a longitudinal axis of orientation with respect to the body of the fetus.

A female fetus, however, does not undergo any significant morphological change of the external genitalia. The clitoris remains a structure bound down by the clitoral hood and thus continues to be in a longitudinal axis of orientation, rather than a structure which points away from the body contour.

Labio-scrotal fold fusion is the key process which results in the development of the male pattern. This is distinct from the pattern of the fetus in the indifferent stage of development, as well as being different from the fetus with female genetic potential.

FIG. 1 shows a male fetus (FIG. 1A) as being indistinguishable from a female fetus (FIG. 1B) during the tenth to twelfth weeks of gestation. As labio-scrotal fold fusion occurs, however, the male fetus becomes increasingly identifiable as a male and at the same time becomes distinguishable from a female, as shown by a comparison between FIGS. 1C and 1D. This process occurs during the twelfth to fourteenth weeks of gestational age. Fetal anatomic sex assignment is therefore achievable during the twelfth to fourteenth weeks of gestational age.

The present invention provides a method and apparatus for performing ultrasonic fetal anatomic sex assignment during early pregnancy with substantially 100 percent accuracy. A typical obstetric ultrasound examination requires about 10 minutes. During this time, the ultrasound transducer is scanned over the womb of the mother. The ultrasound, however, is pulsed on and off. The ultrasound pulses are short and infrequent, and the energy projected by good quality ultrasound equipment is minimal. Assuming the maximum exposure of any given portion of the fetus is one minute, the volume of tissue is exposed to ultrasound by typical ultrasound equipment for a total of less than one-thousandth of a second, and the entire fetus is exposed for less than one-hundredth of a second. Consequently, there is no known danger to the fetus.

The ultrasound equipment preferably used is Hitachi Linear Array Model EUB-27 high resolution digital linear-array real-time ultrasound. However, the same accuracy can be achieved with Hitachi Linear Array Model EUB-25M, Picker International LS3000, and Diasonics DLA100. The digital linear-array real-time ultrasound equipment, as compared to the earlier analog ultrasound equipment, has a capability of imaging resolution to achieve accurate fetal anatomic sex assignment. Software resident in this ultrasound equipment delineates the correlation between the embryological fetal anatomy and the ultrasonic imaging such that the accuracy which can be obtained when performing external genitalia sex assignment in weeks 12 to 14 of gestation using ultrasound is comparable to the accuracy of genetic amniocentesis performed during the fourth month of pregnancy.

Ultrasonic fetal anatomic sex assignment during early pregnancy was originally developed in mothers undergoing an ultrasound examination in conjunction with a medically indicated genetic amniocentesis in the gestational age range of 16 to 18 weeks. Two ultrasound scans are preferably performed, the second being the final determining diagnosis, particularly in the case of diagnosis of female. Males can be identified in the twelfth week of gestation. Females can be provisionally identified in the twelfth week with a second confirmatory ultrasound scan preferably performed two weeks later within the gestational age range of 12 to 14 weeks. The mother's last menstrual period date and the fetal measurement profile, that is, biparietal diameter (BPD) and the femur length, are used for verification that the gestational age range is 12 to 14 weeks.

A male fetus can be identified in the twelfth week of gestation and prior to completion of the fourteenth week of gestation, because the recognition of a male arises from being able to visualize that morphological developmental pattern which is different from a female. As the male external genitalia change from the indifferent stage of development, the diagnosis of male can be achieved merely by pattern recognition and is not dependent upon the visualization process being repeated during a defined gestational stage of development as is preferable for identification of a female fetus. The genetic potential for male is expressed during the twelfth week of gestation. A male undergoes labio-scrotal fold fusion with subsequent elevation of the genital tubercle into its position as the penis during the twelfth week of gestation.

A female does not significantly change from the indifferent stage of development. The female external genitalia merely undergo growth and enlargement without any significant morphological change. It is a relative lack of change from the indifferent stage of development that characterizes the female. Hence, it is preferable to demonstrate a provisional fetal anatomic sex assignment of females and to confirm the provisional demonstration of female a second time two weeks later, that the biological or genetic potential inherent for male is not going to be expressed because of either biological variation in the maturation process, a dating error according to the last menstrual period of the mother, or an error in measurement techniques, that is, BPD and femur length measurements which have a prediction range of error plus or minus seven to ten days when performed in the gestational age range of 12 to 14 weeks.

Specificity and sensitivity of the method of ultrasonic fetal anatomic sex assignment in accordance with the invention are enhanced by actively excluding the opposite sex when an assignment is made. The capability of real-time ultrasound to rapidly repeat the diagnostic evaluation to verify the sex assignment, as well as to rule out the opposite sex assignment, in different planes of orientation contributes to the demonstrated statistic of substantially 100 percent accuracy.

Considered in more detail, the genital area of a fetus is preferably ultrasonically imaged with the genital structure visualized in two ultrasonic scan planes of orientation, as shown in FIG. 2. Preferably, one of the ultrasonic scan planes, referred to as the first ultrasonic scan plane and labeled scan plane #1 in FIG. 2, is a transverse scan plane. The transverse ultrasonic scan plane can be described as a plane perpendicular to the spinal column of the fetus and tangent to the external genitalia of the fetus. Stated differently, visualize that the fetus is seated on a rigid planar surface with the torso perpendicular to the thighs, that is, with the back straight. The first or transverse ultrasonic scan plane corresponds to the plane of the rigid planar surface. Another ultrasonic scan plane, referred to as the second ultrasonic scan plane and labeled scan plane #2 in FIG. 2, is a longitudinal scan plane. The longitudinal ultrasonic scan plane can be described as a plane which bisects the body of the fetus along the longitudinal axis of the fetus through the external genitalia and the spinal column.

FIG. 2 shows transducer placements on the maternal abdomen used to ultrasonically image a fetus between the thighs as seen in ultrasonic scan plane #1 and to ultrasonically image the fetus sagittally through the longitudinal axis of the fetal body to obtain ultrasonic scan plane #2. Once a provisional ultrasonic fetal anatomic sex assignment is made in one ultrasonic scan plane of orientation, ultrasonic imaging is preferably continued in the other alternative ultrasonic scan plane of orientation to assure the opposite sex has been excluded.

As shown in FIG. 2, preferably a transducer 20 for obtaining an ultrasonic image in ultrasonic scan plane #1 and for alternatively obtaining an ultrasonic image in ultrasonic scan plane #2 for the purpose of assigning fetal anatomic sex is indicated by way of illustration. The transducer 20 is preferably used for obtaining an ultrasonic image initially in ultrasonic scan plane #1 and subsequently in ultrasonic scan plane #2.

The transducer 20 is connected by a cable 22 to high resolution digital linear-array real-time ultrasound equipment 24, such as Hitachi Linear Array Model EUB-27 or EUB-25M. The ultrasound equipment 24 includes a display 26, such as a cathode ray tube, for displaying an ultrasonic image in real-time. A single frame ultrasonic image which appears on the display 26 can be electronically frozen and photographed by means of a Polaroid (registered trademark) camera, for example, or the entire real-time examination videotape recorded for later review, as well as record keeping.

FIGS. 3C and 3D are schematic diagrams of the accompanying Polaroid photographic images of typical ultrasound scans showing prominent male and female external genitalia patterns in FIGS. 3A and 3B, respectively, as ultrasonically imaged in ultrasonic scan plane #1 shown in FIG. 2. Furthermore, FIGS. 4C and 4D are schematic diagrams of the accompanying Polaroid photographic images of typical ultrasound scans showing prominent male and female external genitalia patterns in FIGS. 4A and 4B, respectively, as ultrasonically imaged in ultrasonic scan plane #2 shown in FIG. 2. The Polaroid film documentations were obtained from fetuses in the fourteenth week of gestation.

The diagnosis of male is made by identifying the male external genitalia as a two component structure when visualized in ultrasonic scan plane #1. It is comprised of a bright single echo which represents the penis and two less bright echoes side-by-side, visualized at a distance below the penis, which represent the fused labio-scrotal folds and evidence the early stage of formation of the testicle sac, as shown in FIGS. 3A and 3C.

The diagnosis of female is made by identifying the female external genitalia as a three component structure when visualized in ultrasonic scan plane #1. It is comprised of a rectangular echo located between two parallel linear echoes, as shown in FIGS. 3B and 3D. The two thinner less bright lateral echoes represent the unfused labio-scrotal folds which later form the labia majora. The central rectangular brighter echo represents the clitoris.

In ultrasonic scan plane #2, the male genital structure is visualized similarly to the visualization in ultrasonic scan plane #1, that is, a bright single echo which represents the penis and two less bright echoes side-by-side, visualized at a distance below the penis, which represent the fused labio-scrotal folds and evidence the early stage of formation of the testicle sac, as shown in FIGS. 4A and 4C. The axis of the bright single echo which represents the penis elevates from an axis parallel to the spinal column into an axis perpendicular to the spine as the penis develops. In ultrasonic scan plane #2, the female genital structure is visualized as only one structure which comprises a rectangular structure, as shown in FIGS. 4B and 4D. It is visualized as being a prominent echo which is in the same line of continuity as the lower abdominal wall of the fetus and protrudes out from the pubic region pointing in a direction which maintains an orientation parallel to the axis of the spinal column, as shown in FIGS. 4B and 4D. It is this directional difference which permits the ultrasonologist to provisionally make an early ultrasonic fetal anatomic sex assignment.

Visualization in both ultrasonic scan planes of orientation permits differentiating the male pattern from the female pattern. These details thereby assure the accuracy of the final ultrasonic fetal anatomic sex assignment.

Preferably, two ultrasound scans are performed two weeks apart in the twelfth to fourteenth weeks of gestation according to the last menstrual period dating and fetal measurement profile dating. This provides assurance that the two visualization studies are performed during the period of 12 to 14 weeks of gestation. Most males manifest the male pattern during the twelfth week. The purpose of the second ultrasound scan in the fourteenth week is to verify the provisional visualization study of fetal anatomic sex performed in the twelfth week. Verification is particularly important in the case that the provisional visualization study indicates a female fetus. This is desirable due to biological variation, that is, the genetic potential for male might not be manifested in the twelfth week. Consequently, the fetus can appear female, that is, the same as in the indifferent stage of development, but eventually the male pattern appears as the true genetic potential for male is expressed in the thirteenth to fourteenth weeks of gestation. Fusion of the labio-scrotal folds forces the genital tubercle, which is developing into the shaft of the penis by incorporation of the urethra, into an orientation away from the initial orientation parallel to the spinal column. The fetus with the potential of developing male external genitalia exhibits a bright single echo which represents the genital tubercle destined to become the penis. It skews farther away from an orientation initially parallel to the spinal column of the fetus to an orientation at a right angle to the spine. The penis becomes a relatively prominent structure.

In the case of a fetus with female external genitalia, the central rectangular echo which represents the clitoris becomes less distinct and appears to recede relative to the two less bright lateral echoes which represent the labia majora. This is due to the fact that the clitoris is bound down by the clitoral hood. It does not incorporate the urethra and therefore is a relatively less prominent structure overall compared to the echo which represents the penis of a male fetus. Consequently, the growth of the tissue which forms the labia majora enlarges relative to the clitoris which creates the appearance that the clitoris of the female seems to recede as compared to the penis of a male which becomes more prominent. It should be noted, however, that recognition of the development of fetal external genitalia by performance of a series of ultrasound scans is not required after the fourteenth week, since the basic differences in the characteristics of the ultrasonic images produced by male external genitalia and female external genitalia, respectively, continue in evidence for the remainder of gestation.

Ultrasonic fetal anatomic sex assignment in accordance with the invention has been conducted during the sixteenth to eighteenth weeks of gestation in 400 consecutive cases of mothers who have undergone genetic amniocentesis. The results are as follows.

Four hundred mothers who underwent indicated genetic amniocentesis had gestational age confirmed by obtaining concordance of last menstrual period dates with both BPD and femur length measurements. Ultrasonic fetal anatomic sex assignment was performed as a routine part of the fetal anatomic survey to exclude structural abnormalities. These studies were performed using digital linear-array real-time ultrasound equipment, such as Hitachi Linear Array Model EUB-25M.

The time needed to complete sex assignment varied from 30 seconds to 10 minutes. Duration was a function of image quality, which was unaffected by fetal position, but affected by the thickness of the maternal abdominal wall and anterior localization of the placenta.

The time needed to complete ultrasonic fetal anatomic sex assignment varied from 10 to 60 seconds in each thin mother and also in each mother with a posterior located placenta. This increased to 10 minutes in each obese mother and also in each mother who was both obese and who had an anterior located placenta.

In one case among the first 100 mothers studied, discordance was noted at the time of the initial chromosome analysis laboratory report. Subsequent reassessment of the patient file karyotype revealed that a clerical error in reporting had been made by the laboratory. The ultrasonic fetal anatomic sex assignment was actually concordant with the patient file karyotype. The mother was recontacted and informed that the ultrasonic fetal anatomic sex assignment was correct and concordant with the actual chromosome analysis.

Follow-up information on the sex of the infants at birth is ongoing. No infant has been born with discordance between ultrasonic fetal anatomic sex assignment and the chromosome analysis or with external genitalia ambiguity. In the subsequent 300 cases, there was a correct prenatal diagnosis of sex reversal in the form of testicular feminization syndrome. In this subsequent group of 300 cases, there was also one case of sex chromosome mosiacism in the amniotic fluid culture and one case of ambiguous sex chromosomes. The former was a case of 45XO/46XY, which implies ambiguous external genitalia, but by ultrasound was a male. The aborted fetus was a male with no evidence of external genitalia ambiguity the latter case was 46XX, 15pt de novo y, which implies a male with Klinefelter's syndrome, but by ultrasound was a female. The pregnancy was continued in light of the ultrasound visualization study, and a normal female has been born.

In the later 300 cases of ultrasonic fetal anatomic sex assignment, a change in protocol was introduced. The chromosome analysis laboratory requested blood to be drawn from each mother at the time of genetic amniocentesis. The objective was to check the maternal blood chromosome polymorphisms against those of the fetus. This was done only when the sex chromosomes showed a female. The purpose of this fingerprinting technique was to confirm that a difference existed between a mother's chromosomes and her female fetus' to eliminate the possibility that only the mother's chromosomes had been tested having grown from cells of a piece of skin contaminant obtained as the needle passed through maternal tissue while accessing the amniotic fluid cavity. This skin contamination when mixed with the amniotic fluid can overgrow all the actual fetal amniotic fluid cells. The testing then of chromosomes is of the mother and not of the female fetus. An implication is that a fetus having a potential for Down syndrome can be missed. Demonstrating the different fingerprint pattern of chromosome polymorphisms of the chromosomes obtained from the genetic amniocentesis and those obtained from the mother's blood proves that a female fetus was tested. This, of course, cannot occur when the fetal sex chromosomes obtained are male.

This technique offered the opportunity to set up a study whereby the sex of the fetus would be prospectively identified before knowing the sex chromosome result. In order to avoid drawing blood unnecessarily and to eliminate performing a blood chromosome analysis on the mother unnecessarily, if the fetus was a male, agreement was reached that when the ultrasonic fetal anatomic sex assignment revealed a male fetus, no maternal blood was to be drawn for maternal blood chromosome analysis. This added a perspective to the performance of ultrasonic fetal anatomic sex assignment. Accuracy of the ultrasonic fetal anatomic sex assignment was 100 percent in this subsequent group of 300 cases, except as noted.

Subsequently, another 100 mothers scheduled for genetic amniocentesis have had ultrasound scans performed in the twelfth to fourteenth weeks of gestation. The same 100 percent accuracy continues to be achieved at this earlier stage of gestation.

The attainment of 100 percent accuracy of ultrasonic fetal anatomic sex assignment by digital linear-array real-time ultrasonic imaging provides the obstetrician geneticist with data applicable to prenatal diagnosis case management situations for X-linked disorders. Elimination of genetic amniocentesis can be considered for sex determination in those situations which involve prenatal diagnosis of X-linked disorders where a female is identified. For instance, genetic amniocentesis can be eliminated in genetic counseling associated with Duchenne muscular dystrophy. Also, in the case of a family having male relatives with X-linked hydrocephalus, identification of a female by ultrasonic fetal anatomic sex assignment can reduce both the risk of recurrence, as well as provide reassurance to the mother. On the other hand, by identifying a male, which is at increased risk for recurrence, the physician can monitor for hydrocephalus more closely. It is then possible from an earlier stage of gestation to monitor ventricular development, looking for early abnormal ventricle enlargement prior to the twentieth week of gestation. In hemophilia A prenatal diagnosis, the typical genetic amniocentesis just to identify the sex of the fetus can be eliminated. The only need for an invasive procedure (fetoscopy blood sampling) can be performed based on the ultrasonic fetal anatomic sex assignment of male if the prospective parents wish to choose to test the male fetus for the disorder. Generally, in those situations for which there is a biochemical prenatal diagnostic test for an affected male, only the ultrasonic fetal anatomic sex assigned male would require genetic amniocentesis, such as in the case of a family history of Hunter's syndrome, Lesch-Nyhan syndrome, or adrenoleukodystrophy.

Only by the routine use of ultrasonic fetal anatomic sex assignment can the prenatal diagnosis of sex chromosome reversal in amniotic fluid cultures be made, for example, the detection of a 46,XX male fetus or a 46,XY testicular feminization female. Additional testing of the amniotic fluid for testosterone levels (Judd, H. L., Robinson, J. E., Young, P. E., Jones, O. W., "Amniotic Fluid Testosterone Levels in Mid Pregnancy," Obstetrics and Gynecology, Vol. 48, 6 (Dec., 1976)) and finding the levels to be high in the male range does not detect the presence of sex reversal. In the absence of the combination of ultrasonic fetal anatomic sex assignment with genetic amniocentesis, these cases would not be identified until after delivery. At that time, sex reversal could conceivably be dismissed as a clerical error unless a repeat chromosome test is performed on the infant.

In accordance with the invention, both an ultrasonic scan and genetic amniocentesis are needed to ascertain the presence of testicular feminization in the prenatal diagnosis gestational age range. Testicular feminization is an example of true sex reversal as evidenced by the fact that the chromosomes of the fetus are male. There is, however, a testosterone receptor blockage. Consequently, the fetus responds only to female hormones, namely, estrogen, and develops as a female with female external genitalia. Such a protocol not only enables the prenatal diagnosis of testicular feminization, but also can clarify genetic counseling in other situations which involve ambiguous sex chromosomes, such as sex chromosome mosaicism, for example, 45,XO/46,XY (these have all been found to be phenotypical males), 46,XX 15p+ shown to be a de novo Y translocation by Q and C banding, which chromosomally is the same as 47,XXY (these are abnormal males with Klinefelter's syndrome). By visualizing female external genitalia, it can be implied at the time of the prenatal diagnosis that the fetus does not have Klinefelter's syndrome. The fetus by ultrasound scan appears as a normal female. The clarification for the purpose of genetic counseling in this latter situation has significance in further validating the benefit of ultrasonic fetal anatomic sex assignment by visualization of the female external genitalia in conjunction with genetic amniocentesis. The ultrasound becomes the more important clarifying diagnostic component of the process of prenatal diagnosis and in effect takes precedence over the chromosome analysis which implies ambiguity. The couple can be counseled to ignore the apparent abiguity of the chromosome analysis and to expect a normal female infant.

In any event, consideration can be given to the routine performance of ultrasonic fetal anatomic sex assignment in genetic amniocentesis programs. This can facilitate prenatal diagnosis case management and help to discover clerical errors committed by a chromosome analysis laboratory.

Fetal anatomic sex assignment (that is, in the gestational age range of 12 to 14 weeks) by visualization of the external genitalia with ultrasonic imaging is applicable not only to X-linked medical genetic counseling situations, but also to the prenatal chorionic villous biopsy diagnosis technique (CVB). CVB is a new medical biopsy technique and is performed at an early stage of gestation (8 to 10 weeks). There is a risk that the tissue sampled can be maternal, rather than a sample of the placenta chorionic villi which constitutes only fetal tissue. The presence of maternal tissue in the sample obtained by biopsy causes a risk of sex determination based only on a chromosomal analysis which can be of maternal tissue, rather than on the basis of the fetal tissue. This can cause an error. An ultrasound scan in accordance with the invention in the gestational age range of 12 to 14 weeks can confirm the sex chromosome determination made by means of CVB at the earlier stage of gestation.

If CVB is performed for an X-linked indication, the pregnancy can be continued when a female is diagnosed. The phenotypic sex can be verified so that the possibility of maternal contamination is excluded by using ultrasonic imaging to verify that the fetus is a female. A chromosome analysis of 46,XX female and a determination using ultrasonic imaging that the fetus is a male establishes that the analysis was a maternal cell contamination. If the fetus is a female, it would not exclude the possibility that the sex chromosome determination was in fact the mother's. However, by verifying that a female fetus is the ongoing product of the pregnancy, at least a misdiagnosis of missed male would not occur. This is vitally important because females who might be carrying the X-linked disorder gene are unaffected, but males who carry the X-linked disorder gene are affected. If the fetus is a male, additional testing must then be done on the male, if the parental desire is to have an unaffected infant born or identify an affected male.

There is an anatomic corollary to ambiguous sex chromosomes. Ultrasonic fetal anatomic sex assignment can be potentially useful in the evaluation of the fetus at risk for, or who has, external genitalia ambiguity, such as congenital adrenal hyperplasia (masculinized female genitalia) and in the potential of visualization of external genitalia which appear to be ambiguous, such as can be expected in varying degrees of hypospadius and other rare cases of incomplete genital development. If one of these situations is suspected by ultrasonic fetal anatomic sex assignment in an ultrasound scan, genetic amniocentesis can then be performed for sex chromosome analysis to assist genetic counseling of anticipated sex assignment.

A wider source of benefit of an accurate noninvasive procedure for accurate fetal sex assignment can be in providing enhancement of the maternal and/or paternal bond with the developing fetus. Improving the bond makes ultrasonic fetal anatomic sex assignment a potentially important tool in pregnancy health care if it can encourage the reduction or elimination of fetal hazards, such as maternal ingestion of alcohol, illicit drugs, smoking, etc.

While various embodiments of the ultrasonic fetal anatomic sex assignment method and apparatus for use during early pregnancy have been described in order to make the invention understandable to those skilled in the art, it will be appreciated that variations and modifications not mentioned will become apparent to those skilled in the art. It is to be clearly understood that the above description is by way of illustration and example only and is not to be taken by way of limitation. Accordingly, the spirit and scope of this invention are ascertainable only by reference to the appended claims.

What is claimed is:

1. A method for assigning the anatomic sex of a fetus during the twelfth week to the fourteenth week of pregnancy, comprising the steps of:
    ultrasonically imaging the genital area of the fetus during the twelfth week to the fourteenth week of pregnancy in a transverse ultrasonic scan plane;
    diagnosing a male fetus by identifying the male external genitalia as a two component structure comprised of a bright single echo which represents the penis and two less bright echoes sideby-side, visualized at a distance from the penis, which represent the fused labio-scrotal folds and evidence the early formation of the testicle sac; and
    diagnosing a female fetus by identifying the female external genitalia as a three component structure comprised of a rectangular echo located between two parallel linear echoes.

2. The method of claim 1 wherein the step of ultrasonically imaging the genital area of the fetus in the transverse ultrasonic scan plane is repeated during the period of twelve to fourteen weeks of gestation, thereby verifying fetal anatomic sex.

3. The method of claim 1, further comprising the steps of:
    performing sex chromosome sampling on the fetus;
    performing sex chromosome analysis; and
    comparing the diagnosis of fetal anatomic sex assigned by ultrasonically imaging the genital area of the fetus in the transverse ultrasonic scan plane and the sex chromosome analysis based on sex chromosome sampling;
    thereby detecting any discordance of the ultrasonic fetal anatomic sex assignment and the sex chromosome analysis.

4. The method of claim 1, further comprising the steps of:
    ultrasonically imaging the genital area of the fetus during the twelfth week to the fourteenth week of pregnancy in a longitudinal ultrasonic scan plane;
    diagnosing a male fetus by identifying the male external genitalia as a two component structure comprised of a bright signal echo having an axis at substantially a right angle to the axis of the spinal column, which represents the penis, and two less bright echoes side-by-side, visualized at a distance from the penis, which represent the fused labio-scrotal folds and evidence the early formation of the testicle sac; and
    diagnosing a female fetus by identifying the female external genitalia as a rectangular structure comprised of a prominent echo which is in the same line of continuity as the lower abdominal wall and protrudes out from the pubic region pointing in a direction which maintains an orientation parallel to the axis of the spinal column, which represents the clitoris;
    thereby imaging the genital area of the fetus in two alternative scan planes of orientation to assure the opposite fetal anatomic sex has been excluded.

5. The method of claim 4 wherein the steps of ultrasonically imaging the genital area of the fetus in the transverse and longitudinal ultrasonic scan planes are repeated during the period of twelve to fourteen weeks of gestation, thereby verifying fetal anatomic sex.

6. The method of claim 1 wherein the step of ultrasonically imaging the genital area of the fetus with the genital structure visualized in the transverse ultrasonic scan plane comprises the steps of positioning ultrasonic transducer means for ultrasonic imaging in the transverse ultrasonic scan plane, connecting high resolution digital linear-array real-time ultrasound means to the transducer means, and connecting means to the ultrasound means for displaying the genital structure of the fetus in the transverse ultrasonic scan plane.

7. A method for assigning the anatomic sex of a fetus during the twelfth week to the fourteenth week of pregnancy, comprising the steps of:
 ultrasonically imaging the genital area of the fetus during the twelfth week to the fourteenth week of pregnancy in a longitudinal ultrasonic scan plane;
 diagnosing a male fetus by identifying the male external genitalia as a two component structure comprised of a bright single echo having an axis at substantially a right angle to the axis of the spinal column, which represents the penis, and two less bright echoes side-by-side, visualized at a distance from the penis, which represent the fused labio-scrotal folds and evidence the early formation of the testicle sac; and
 diagnosing a female fetus by identifying the female external genitalia as a rectangular structure comprised of a prominent echo which is in the same line of continuity as the lower abdominal wall and protrudes out from the pubic region pointing in a direction which maintains an orientation parallel to the axis of the spinal column, which represents the clitoris.

8. The method of claim 7 wherein the step of ultrasonically imaging the genital area of the fetus in the longitudinal ultrasonic scan plane is repeated during the period of twelve to fourteen weeks of gestation, thereby verifying fetal anatomic sex.

9. The method of claim 1, further comprising the steps of:
 performing sex chromosome sampling on the fetus;
 performing sex chromosome analysis; and
 comparing the diagnosis of fetal anatomic sex assigned by ultrasonically imaging the genital area of the fetus in the longitudinal ultrasonic scan plane and the sex chromosome analysis based on sex chromosome sampling;
 thereby detecting any discordance of the ultrasonic fetal anatomic sex assignment and the sex chromosome analysis.

10. The method of claim 1 wherein the step of ultrasonically imaging the genital area of the fetus with the genital structure visualized in the longitudinal ultrasonic scan plane comprises the steps of positioning ultrasonic transducer means for ultrasonic imaging in the longitudinal ultrasonic scan plane, connecting high resolution digital linear-array real-time ultrasound means to the transducer means, and connecting means to the ultrasound means for displaying the genital structure of the fetus in the longitudinal ultrasonic scan plane.

11. A method for assigning the anatomic sex of a fetus during the twelfth week to the fourteenth week of pregnancy, comprising the steps of:
 ultrasonically imaging the genital area of the fetus during the twelfth week to the fourteenth week of pregnancy in a first ultrasonic scan plane;
 diagnosing a male fetus by identifying the male external genitalia in the first ultrasonic scan plane as a two component structure comprised of a bright single echo which represents the penis and two less bright echoes side-by-side, visualized at a distance from the penis, which represent the fused labio-scrotal folds and evidence the early formation of the testicle sac;
 diagnosing a female fetus by identifying the female external genitalia in the first ultrasonic scan plane as a three component structure comprised of a rectangular echo located between two parallel linear echoes;
 ultrasonically imaging the genital area of the fetus during the twelfth week to the fourteenth week of pregnancy in a second ultrasonic scan plane;
 diagnosing a male fetus by identifying the male external genitalia in the second ultrasonic scan plane as a two component structure comprised of a bright single echo having an axis at substantially a right angle to the axis of the spinal column, which represents the penis, and two less bright echoes side-by-side, visualized at a distance from the penis, which represent the fused labio-scrotal folds and evidence the early formation of the testicle sac; and
 diagnosing a female fetus by identifying the female external genitalia in the second ultrasonic scan plane as a rectangular structure comprised of a prominent echo which is in the same line of continuity as the lower abdominal wall and protrudes out from the pubic region pointing in a direction which maintains an orientation parallel to the axis of the spinal column, which represents the clitoris;
 thereby imaging the genital area of the fetus in two alternative ultrasonic scan planes of orientation to assure the opposite fetal anatomic sex has been excluded.

12. The method of claim 11 wherein the first ultrasonic scan plane is a transverse ultrasonic scan plane.

13. The method of claim 11 wherein the second ultrasonic scan plane is a longitudinal ultrasonic scan plane.

14. The method of claim 11 wherein the steps of ultrasonically imaging the genital area of the fetus in the first and second ultrasonic scan planes are repeated during the period of twelve to fourteen weeks of gestation, thereby verifying fetal anatomic sex.

15. The method of claim 11, further comprising the steps of:
 performing sex chromosome sampling on the fetus;
 performing sex chromosome analysis; and
 comparing the diagnosis of fetal anatomic sex assigned by ultrasonically imaging the genital area of the fetus in the first and second ultrasonic scan planes and the sex chromosome analysis based on sex chromosome sampling;
 thereby detecting any discordance of the ultrasonic fetal anatomic sex assignment and the sex chromosome analysis.

16. The method of claim 11 wherein the steps of ultrasonically imaging the genital area of the fetus with the genital structure visualized in the first and second ultrasonic scan planes comprise the steps of positioning ultrasonic transducer means for ultrasonic imaging alternatively in the first and second ultrasonic scan planes, connecting high resolution digital linear-array real-time ultrasound means to the transducer means, and connecting means to the ultrasound means for displaying the genital structure of the fetus in the first and second ultrasonic scan planes.

17. A method for ascertaining instances of testicular feminization and cases of sex chromosome mosaicism during pregnancy, comprising the steps of:

assigning fetal anatomic sex by ultrasonically imaging the genital area of the fetus with the genital structure visualized in at least one ultrasonic scan plane;

performing genetic amniocentesis on the fetus; and comparing the diagnosis of fetal anatomic sex assigned by ultrasonically imaging the genital area of the fetus with the genital structure visualized in the at least one ultrasonic scan plane and the sex chromosome analysis determined by genetic amniocentesis;

thereby detecting any discordance of the ultrasonic fetal anatomic sex assignment and the chromosome analysis to ascertain instances of testicular feminization and cases of sex chromosome mosaicism.

18. A method for associating the results of ultrasonic imaging and chromosome analysis on a fetus, comprising the steps of:

assigning fetal anatomic sex by ultrasonically imaging the genital area of the fetus during the twelfth week to the fourteenth week of pregnancy in at least one ultrasonic scan plane;

performing sex chromosome analysis on a sample of at least one of fetal material and amniotic material; and comparing the assignment of fetal anatomic sex determined by ultrasonic imaging and the sex chromosome analysis;

so that any discordance between the ultrasonic fetal anatomic sex assignment and the sex chromosome analysis is detected.

19. The method of claim 18 wherein the at least one ultrasonic scan plane is a transverse ultrasonic scan plane.

20. The method of claim 18 wherein the at least one ultrasonic scan plane is a longitudinal ultrasonic scan plane.

* * * * *